(12) United States Patent
Karjalainen et al.

(10) Patent No.: US 6,479,530 B2
(45) Date of Patent: Nov. 12, 2002

(54) IMIDAZOLE DERIVATIVES HAVING AFFINITY FOR $\alpha_2$ RECEPTORS

(75) Inventors: Arto Karjalainen, Espoo (FI); Paavo Huhtala, Espoo (FI); Juha-Matti Savola, Turku (FI); Siegfried Wurster, Turku (FI); Maire Eloranta, Oulu (FI); Maarit Hillilä, Piispanristi (FI); Raimo Saxlund, Multia (FI); Victor Cockcroft, Turku (FI); Arja Karjalainen, Espoo (FI)

(73) Assignee: Orion Corporation, Espoo (FI)

(*) Notice: Subject to any disclaimer, the term of this patent is extended or adjusted under 35 U.S.C. 154(b) by 0 days.

(21) Appl. No.: 09/904,836

(22) Filed: Jul. 16, 2001

(65) Prior Publication Data

US 2002/0007074 A1 Jan. 17, 2002

Related U.S. Application Data

(63) Continuation of application No. 09/051,151, filed as application No. PCT/FI96/00518 on Oct. 2, 1996, now Pat. No. 6,313,311.

(30) Foreign Application Priority Data

Oct. 3, 1995 (GB) .............................................. 9520150

(51) Int. Cl.[7] .................. A61K 31/4164; C07D 233/58; C07D 233/64

(52) U.S. Cl. ..................... 514/396; 514/400; 548/341.1; 548/345.1

(58) Field of Search ........................ 548/345.1, 341.1; 514/396, 400

(56) References Cited

U.S. PATENT DOCUMENTS

| | | | |
|---|---|---|---|
| 3,636,002 A | 1/1972 | Godefroi | 548/345.1 |
| 4,510,149 A | 4/1985 | Cozzi et al. | 514/341 |
| 4,634,705 A | 1/1987 | Debernardis et al. | 514/256 |
| 4,659,730 A | 4/1987 | Hirsch et al. | 514/396 |
| 4,689,339 A | 8/1987 | Karjalainen et al. | 514/396 |
| 4,994,103 A | 2/1991 | De Bouyn et al. | 548/345.1 |
| 5,026,868 A | 6/1991 | Karjalainen et al. | 548/346 |
| 5,204,364 A | 4/1993 | Carganico et al. | 514/399 |
| 5,658,938 A | 8/1997 | Geerts et al. | 514/400 |
| 6,388,090 B2 * | 5/2002 | Huhtala et al. | 548/311.1 |

FOREIGN PATENT DOCUMENTS

| | | | |
|---|---|---|---|
| EP | 183492 | 6/1986 | |
| EP | 717037 | 6/1996 | |
| WO | 93-13074 | 7/1993 | 548/345.1 |

OTHER PUBLICATIONS

K. Matsumoto et al., "Synthesis and $\alpha_2$–Adrenergic Activities of a New Series of Imidazole Analogs," MEDI–164 (1992).

Baddar F.G. et al, "Phenylpropiolic Acids. Part VI, * The Cyclisation of Dissimilarly Substituted Pheylpropiolic Anhydrides to the Corresponding 1–Phenylnaphthlenes", J. Chem. Soc., 1027–1032 (1959).

Chadwick D.J. and Ngochindo R.I., "2,5–Dilithiation of N–Protected Imidazoles. Syntheses of 2,5–Disubstituted Derivatives of 1–Methoxymethyl–, 1–Triphenylmethyl–, and 1–(N,N–Dimethylsulphonamido)–imidazole", J. Chem. Soc. Perkin Trans. I, 481–486 (1984).

(List continued on next page.)

Primary Examiner—Fiona T. Powers
(74) Attorney, Agent, or Firm—Finnegan, Henderson, Farabow, Garrett & Dunner, L.L.P.

(57) ABSTRACT

Imidazole derivatives of formula I

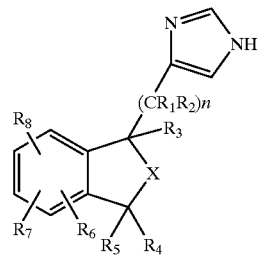

wherein n is 0 or 1, $R_1$ is hydrogen or $C_1$–$C_4$-alkyl, $R_2$ is hydrogen or $R_2$ and $R_3$ together form a double bond, $R_3$ is hydrogen or $C_1$–$C_4$-alkyl or $R_2$ and $R_3$ together form a double bond, $R_4$ is hydrogen, $C_1$–$C_4$-alkyl, hydroxy or $C_1$–$C_4$-alkoxy, $R_5$ is hydrogen or $C_1$–$C_4$-alkyl or $R_4$ and $R_5$ together with the carbon atom to which they are attached form a carbonyl group, $R_6$, $R_7$ and $R_8$ are each the same or different and are independently hydrogen, $C_1$–$C_4$-alkyl or $C_2$–$C_4$-alkenyl, $C_3$–$C_7$-cycloalkyl, hydroxy, $C_1$–$C_4$-alkoxy, $C_1$–$C_4$-hydroxyalkyl, thiol, $C_{1-4}$-alkylthio, $C_{1-4}$-alkylthiol, halogen, trifluoromethyl, nitro or optionally substituted amino, X is —$CHR_9$—$(CHR_{10})_m$—, m is 0 or 1, and $R_9$ and $R_{10}$ are each the same or different and are independently hydrogen or $C_1$–$C_4$-alkyl; or a pharmaceutically acceptable ester or salt thereof, their preparation, use and pharmaceutical compositions comprising them are described. The compounds have affinity for alpha2 receptors and are useful e.g. in the treatment of hypertension, glaucoma, chronic or acute pain, migraine, diarrhea, common cold, ischemia, addiction to chemical substances, anxiety, especially preoperative anxiety and different neurological, musculoskeletal, psychiatric and cognition disorders or as adjuncts to anesthesia.

18 Claims, No Drawings

OTHER PUBLICATIONS

Virtanen R. et al., "High Selective and Specific Antagonism of Central and Peripheral $\alpha_2$–Adrenoceptors by Atipamezole", Arch. Int. Pharmacodyn., 297, 190–204 (1989).

Gregory G.B. et al., "Decyanation of Tertiary Nitriles by Alkyllithium Reagents Observed during the Synthesis of Imidazole Pendant to a Quaternary Carbon Center", J. Org. Chem., 55, 1479–1483 (1990).

Kudzma L.V. and Turnbull S.P. Jr. "Expedient Synthesis of 4(5)–[1–(2,3–Dimethylphenyl)ethyl]–1H–imidazole, the $\alpha_2$–Adrenergic Agonist Medetomidine", Synthesis, 1021–1022 (1991).

Hong S.–S. et al., "A Structure–Activity Relationship Study of Benzylic Modifications of 4–[1–(1–Naphthyl)ethyl]–1H–imidazoles on $\alpha_1$–and $\alpha_2$–Adrenergic Receptors", J. Med. Chem., 37(15), 2328–2333 (1994).

Zhang X., "Design, Synthesis and Biological Activities of 4–Substituted Imidazoles as $\alpha_2$–Adrenoceptor Agonists", Dissertation, The Ohio State University, pp. I–xviii and 1–200 (1995).

Copy of co–pending application No. 09/051,151, Feb. 2, 1999.

* cited by examiner

IMIDAZOLE DERIVATIVES HAVING AFFINITY FOR $\alpha_2$ RECEPTORS

This application is a continuation of application Ser. No. 09/051,151, filed Feb. 2, 1999, now U.S. Pat. No. 6,313,311, which is incorporated herein by reference, and which is a national stage filing of PCT/FI96/00518, filed on Oct. 2, 1996, which published in the English language.

The present invention relates to substituted 4(5)-(1-indanyl and 1-indanylmethyl and 1-indanylmethylen)imidazoles and 4(5)-[1-(1,2,3,4-tetrahydronaphthyl and 1,2,3,4-tetrahydronaphthylmethyl and 1,2,3,4-tetrahydronaphthylmethylen]imidazoles and to their isomers, pharmaceutically acceptable salts and esters. It also relates to their preparation, use and to pharmaceutical compositions containing them.

The compounds of the invention have affinity for alpha2 receptors most of them being very selective alpha2 agonists. Accordingly, they are useful in the treatment of hypertension, glaucoma, migraine, diarrhea, ischemia, addiction to chemical substances (such as tobacco and narcotics) and different neurological, musculoskeletal, psychiatric and cognition disorders as well as sedative and analgesic agents, nasal decongestants, and adjuncts to anaesthesia.

Gregory G. B., et al describe in J. Org. Chem. (1990), 55, 1479–1483 a new synthesis step for 1-phenylalkyl-1-(4-imidazolyl)-1,2,3,4-tetrahydronaphthalene derivatives which are useful as nonpeptide antagonists of the angiotensin II receptor.

The imidazole derivatives of the invention are either compounds of formula I

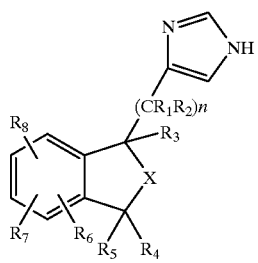

I n is 0 or 1

$R_1$ is hydrogen or $C_1$–$C_4$-alkyl $R_2$ is hydrogen or $R_2$ and $R_3$ together form a double bond $R_3$ is hydrogen or $C_1$–$C_4$-alkyl or $R_2$ and $R_3$ together form a double bond $R_4$ is hydrogen, $C_1$–$C_4$-alkyl, hydroxy or $C_1$–$C_4$-alkoxy $R_5$ is hydrogen or $C_1$–$C_4$-alkyl or $R_4$ and $R_5$ together with the carbon atom to which they are attached form a carbonyl group $R_6$, $R_7$ and $R_8$ are each the same or different and are independently hydrogen, $C_1$–$C_4$-alkyl or $C_2$–$C_4$-alkenyl, $C_3$–$C_7$-cycloalkyl, hydroxy, $C_1$–$C_4$-alkoxy, $C_1$–$C_4$-hydroxyalkyl, thiol, $C_{1-4}$-alkylthio, $C_{1-4}$-alkylthiol, halogen, trifluoromethyl, nitro or optionally substituted amino X is —$CHR_9$—$(CHR_{10})_m$— m is 0 or 1 and $R_9$ and $R_{10}$ are each the same or different and are independently hydrogen or $C_1$–$C_4$-alkyl;

or a pharmaceutically acceptable ester or salt thereof.

The terms as employed herein have the following meanings: A halogen is e.g. chlorine, bromine or fluorine, preferably it is chlorine or fluorine. The $C_1$–$C_4$-alkyl, $C_1$–$C_4$-alkoxy and $C_2$–$C_4$-alkenyl etc. groups may be branched or straight chain groups. $C_3$–$C_7$-Cycloalkyl is a saturated cyclic hydrocarbon group having preferably 3 to 5 carbon atoms. Optionally substituted amino is an amino group which is unsubstituted or substituted with a $C_1$–$C_4$-alkyl group.

When m=n=0

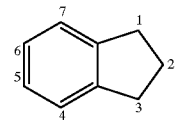

$R_3$ is preferably hydrogen, $R_4$ is preferably hydrogen, hydroxy or $C_1$–$C_4$-alkoxy, such as ethoxy, $R_5$ is preferably hydrogen, or $R_4$ and $R_5$ form, together with the carbon atom to which they are attached, a carbonyl group.

$R_6$ is preferably hydrogen, $C_1$–$C_4$-alkyl or $C_1$–$C_4$-alkoxy, such as methyl, ethyl, t-butyl, methoxy or hydroxy. For example, $R_6$ may be $C_1$–$C_4$-alkyl at position 4, 5 or 6, a $C_1$–$C_4$-alkoxy at position 5, 6 or 7, or hydroxy at position 5 or position 7.

More preferably $R_6$ is hydrogen, 4-methyl, 6-methyl or 7-methoxy.

$R_7$ is preferably at position 5, 6 or 7.

$R_7$ is preferably hydrogen or $C_1$–$C_4$-alkyl, such as, for example methyl or t-butyl. For example $R_7$ may be a $C_1$–$C_4$-alkyl at position 5, 6 or 7, such as 5-methyl, 7-methyl or 6-t-butyl.

More preferably $R_7$ is hydrogen.

$R_8$ is preferably at position 6 or 7.

$R_8$ is preferably hydrogen, hydroxy or $C_1$–$C_4$-alkoxy, such as methoxy. For example, $R_8$ may be a $C_1$–$C_4$-alkoxy at position 6, such as 6-methoxy, or 6-hydroxy or 7-hydroxy.

$R_9$ is preferably hydrogen or methyl.

When n=1 and m=0

$R_1$ is preferably hydrogen or methyl.

$R_2$, $R_3$, $R_4$, $R_5$ and $R_9$ are preferably hydrogen, $R_6$ is preferably hydrogen, halogen, $C_1$–$C_4$-alkyl, $C_1$–$C_4$-alkoxy, such as, for example, methyl or t-butyl, methoxy or hydroxy. $R_6$ is preferably at position 4, 5 or 6. For example, $R_6$ may be a $C_1$–$C_4$-alkyl at position 4, 5 or 6, such as 4- or 5-methyl or 5-t-butyl or a $C_1$–$C_4$-alkoxy at position 5 or 6, such as 5- or 6-methoxy, or 4-, 5- or 6-hydroxy. $R_6$ may be halogen at position 5 or 6, such as 5- or 6-fluoro.

More preferably $R_6$ is 4-, 5- or 6-hydroxy.

$R_7$ is preferably at position 5, 6 or 7.

$R_7$ is preferably hydrogen, $C_1$–$C_4$-alkyl, $C_1$–$C_4$-alkoxy or hydroxyl. For example, $R_7$ may be $C_1$–$C_4$-alkyl at position 5, 6 or 7, such as 5- or 7-methyl or 5- or 6-t-butyl or $C_1$–$C_4$-alkoxy at position 6, such as 6-methoxy, or 6-hydroxy.

More preferably $R_7$ is hydrogen or 6-hydroxy or 6-t-butyl.

$R_8$ is preferably at position 6 or 7.

$R_8$ is preferably hydrogen, hydroxy, $C_1$–$C_4$-alkyl, $C_1$–$C_4$-alkoxy, such as methyl or methoxy, for example $C_1$–$C_4$-alkyl at position 7, such as 7-methyl or 7-t-butyl or $C_1$–$C_4$-alkoxy at position 6, such as 6-methoxy or 6-hydroxy.

When n=m=1

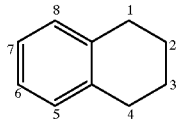

$R_1$, $R_2$, $R_3$, $R_5$, $R_8$, $R_9$ and $R_{10}$ are preferably hydrogen.

$R_4$ is preferably hydrogen or $C_1$–$C_4$-alkyl, such as, for example, methyl.

$R_6$ is preferably at position 5, 6 or 7.

$R_6$ is preferably hydrogen, $C_1$–$C_4$-alkoxy or hydroxy, for example methoxy. For example, $R_6$ may be 5-, 6- or 7-methoxy, or 6- or 7-hydroxy.

$R_7$ is preferably hydrogen or $C_1$–$C_4$-alkyl, such as, for example, t-butyl.

When n=0 and m=1

$R_3$, $R_4$, $R_5$, $R_7$, $R_8$, $R_9$ and $R_{10}$ are preferably hydrogen.

$R_6$ is preferably hydrogen or halogeN, for example chlorine. $R_6$ may be a halogen at position 5, such as, for example 5-chloro.

The invention includes within its scope all the possible isomers and stereoisomers, in particular Z and E (cis and trans isomers) and enantiomers.

The compounds of the formula (I) form acid addition salts with both organic and inorganic acids. Typical acid addition salts are chlorides, bromides, sulfates, nitrates, phosphates, sulfonates, formates, tartrates, maleates, citrates, benzoates, salicylates, ascorbates. Furthermore, compounds wherein one or more of $R_4$ to $R_8$ is a hydroxy group form esters and salts with alkali metals and alkaline earth metals. Typical esters include the lower alkyl esters, such as the methyl, ethyl and propyl esters.

The compounds of the invention may be prepared using the following methods. (It is to be noted that in the formulae below, when the imidazole group is protected, the protecting group R' (benzyl or trityl) may be attached to either of the two nitrogen atoms of the imidazole ring. Accordingly, the use of 1-benzyl-5-imidazolecarbaldehyde as starting material leads to 1.5 substituted derivatives whereas when trityl is used the substitution is mainly 1.4.)

Synthesis of 4(5)-(1-indanyl)imidazoles and the corresponding 4(5)-[1-(1,2,3,4-tetrahydronaphthyl)]imidazoles Method a Compounds of formula I wherein n=0 and m=0 or 1 may be prepared by an acid catalyzed cyclization of protected or unprotected 4(5)-(1-hydroxy-3-phenylpropyl or 1-hydroxy4-phenylbutyl)imidazoles of formulae II and II', respectively.

Accordingly, the 4(5)-(1-indanyl)imidazoles may be prepared by cyclization of the compound of formula II

II

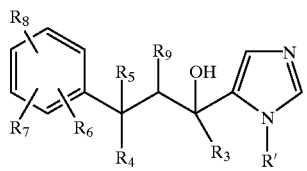

wherein $R_3$ to $R_9$ are as defined above and R' is a protecting group, in the presence of an acid to form the compounds of formula III

III

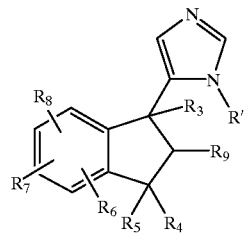

wherein the substituents are as defined above, and removing the protecting group R' to form the compounds of formula Ia Ia

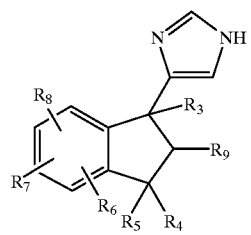

The corresponding 4(5)-[1-(1,2,3,4-tetrahydronaphthyl)]imidazoles may be prepared by cyclization of the compound of II'

II'

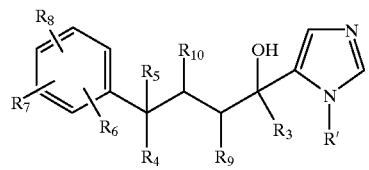

wherein $R_3$ to $R_{10}$ are as defined above I and R' is a protecting group in the presence of an acid to form the compounds of formula III'

III'

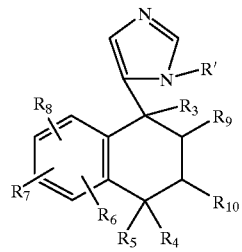

wherein the substituents are as defined above, and removing the protecting group R' to form the compounds of formula Ia'

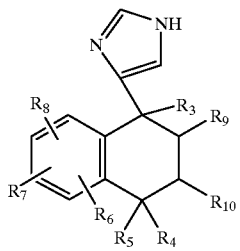

Ia' wherein the substituents are as defined above.

The protecting group R' may be, for example, benzyl or trityl. When R' is trityl it may be removed using an acid and, when it is benzyl, by catalytic hydrogenation. The acid used in the cyclization reaction may be, for example, polyphosphoric acid (PPA) or methanesulfonic acid.

The starting materials (compounds of the formulae II and II', respectively) may be synthesized using different methods. One of them is to prepare α,β-unsaturated ketones through an aldol condensation by allowing an imidazolyl alkyl ketone to react with an appropriately substituted benzaldehyde in the presence of a base:

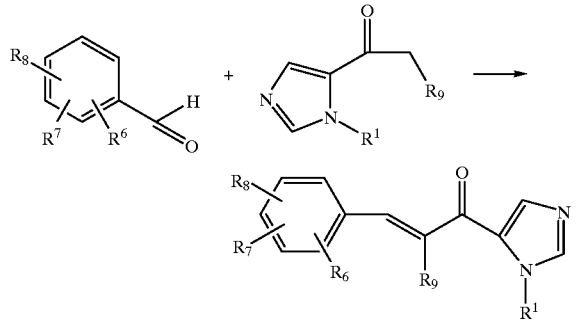

The accompanying reduction of carbonyl and the following catalytic hydrogenation produces saturated alcohols used in the cyclization. The reduction of the carbonyl group may be performed for example with sodium borohydride. If the imidazole moiety has been substituted with the benzyl group it may also be removed by catalytic hydrogenation.

To accomplish substitution at the position 1 of the indane or 1,2,3,4-tetrahydronaphthalene ring it is possible to carry out an 1,2-addition reaction of the intermediate ketone with a nucleophile before the hydrogenation. This is conveniently performed through the Grignard reaction which is carried out by adding to the reaction mixture an alkyl magnesium halide, e.g. bromide, made from alkyl halide and magnesium:

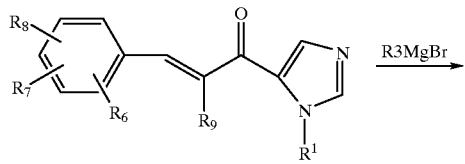

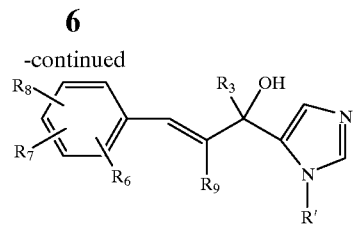

Another useful method to produce appropriate alcohols needed as starting materials in the cyclization is the use of the Grignard reaction in the preparation of 4(5)-(1-hydroxyphenylalkyl)imidazoles. Here the 4(5)-imidazole carbaldehyde or ketone is allowed to react with a Grignard reagent, prepared from appropriately substituted phenylalkyl halide and magnesium:

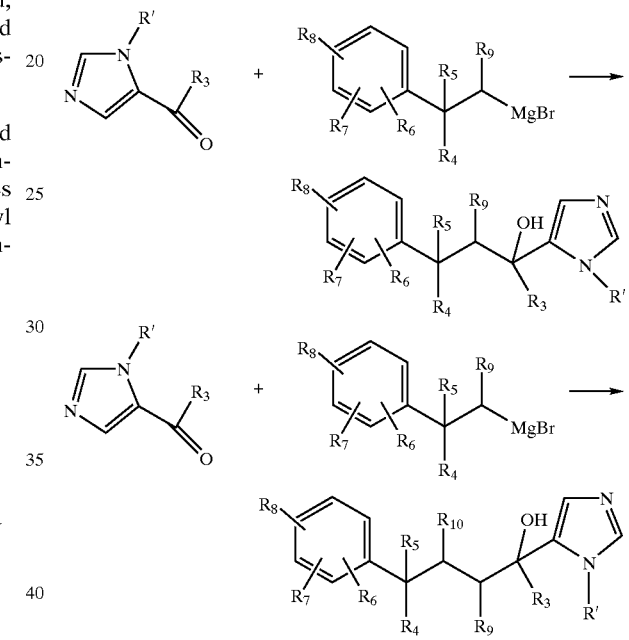

Method b

To obtain substitution at the position 3 of the indane group the following procedure may be used: An intermediate of formula Ib, which is also an active compound wherein $R_4$ and $R_5$ together form a carbonyl group, is prepared.

Ib

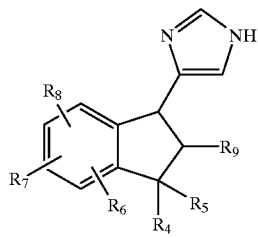

There are different methods for the preparation of this intermediate.

Firstly, it may be prepared using an acid catalyzed cyclization of 1-aryl-3-[4(5)-imidazolyl]-α,β-unsaturated-1-propanones:

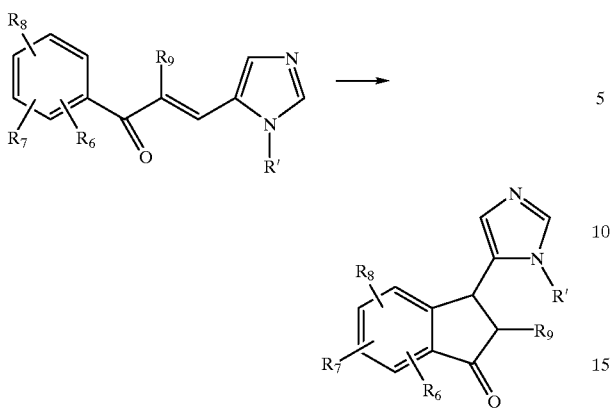

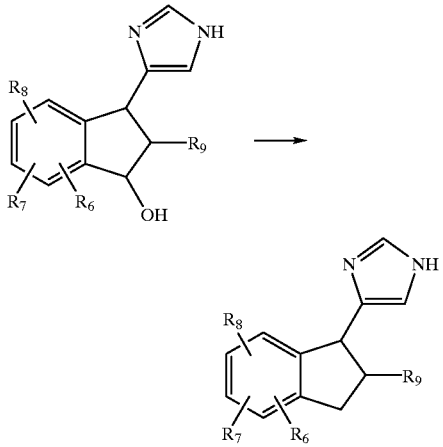

The α,β-unsaturated ketone used as the starting material in the above reaction may be prepared by a base catalyzed aldol condensation from substituted or unsubstituted 4(5)-imidazole carbaldehyde and from appropriately substituted phenyl alkyl ketone.

Secondly, it may be prepared through the condensation of benzyl protected urocanic acid with an appropriately substituted benzene:

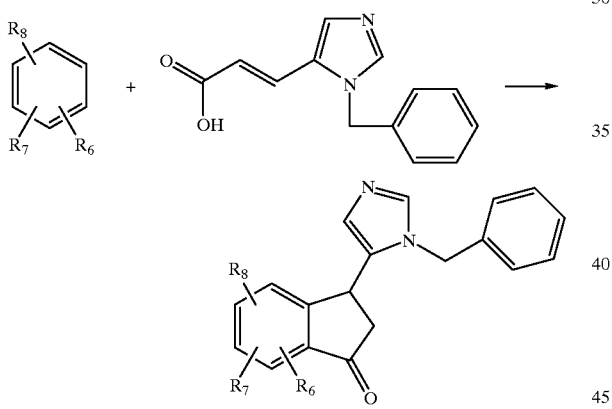

The benzyl protection is abolished by hydrogenation as described earlier.

The ketone group may be then further modified using different methods. It may be reduced to the corresponding alcohol with sodium borohydride or by catalytic hydrogenation, whereafter the alcohol may be hydrogenated:

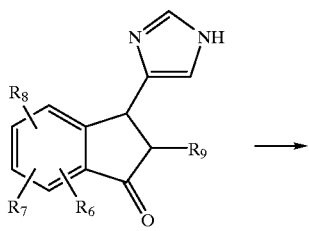

It is also possible to modify the ketone group using Grignard reaction:

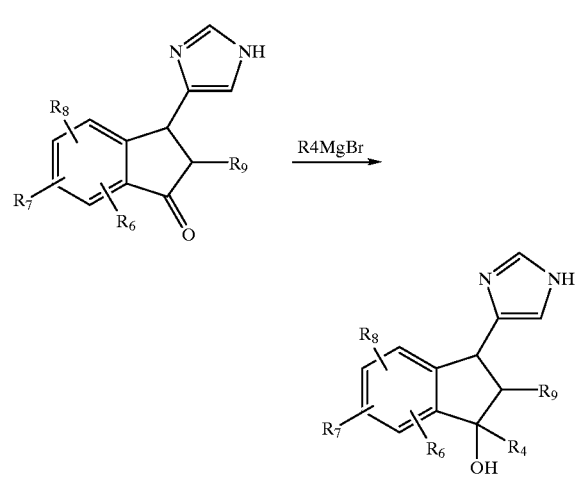

These compounds may be further transformed to compounds of formula I wherein n=m=0 and $R_4$ is an alkyl and $R_5$ is hydrogen by catalytic hydrogenation as described above.

The compounds of formula Ib wherein $R_4$ is alkoxy and $R_5$ is hydrogen may be prepared from the corresponding alcohol in concentrated hydrochloric acid.

Method c

A further method to synthesize the 4(5)-(1-indanyl) imidazoles of the formula I is to use the lithiated imidazole in an aromatic electrophilic substitution reaction with an 1-indanone (imidazole being bis-protected according to the method described by Kudzma et al. in Synthesis, (1991), p. 1021). The protection may be removed by acid treatment, which induces the simultaneous loss of water. The double bond is reduced by catalytic hydrogenation as described above.

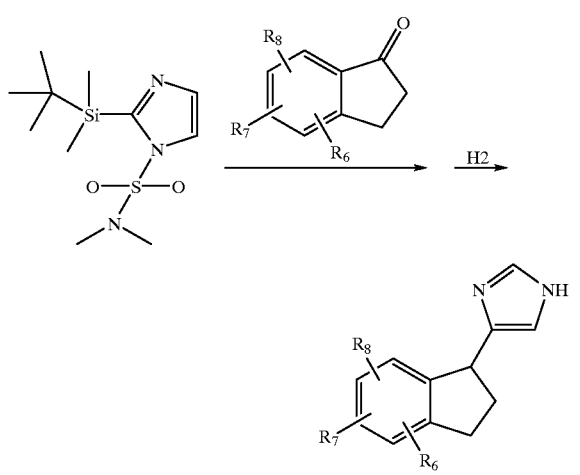

Syntehesis of 4(5)-(indan-1-ylmethyl)imidazoles and 4(5)-(indan-1-ylmethylen)imidazoles and the corresponding tetrahydronaphthyl derivatives Method d The preparation of 4(5)(indan-1-ylmethyl and indan-1-ylmethylen)imidazole and the corresponding tetrahydronaphthyl skeleton may be accomplished using the so called McMurry reaction, in which an imidazole carbaldehyde or ketone reacts with an 1-indanone. The reaction is catalyzed by low valence titanium. The condensation may be followed by the hydrogenation of the double bond and simultaneous elimination of the protecting group in the imidazole ring.

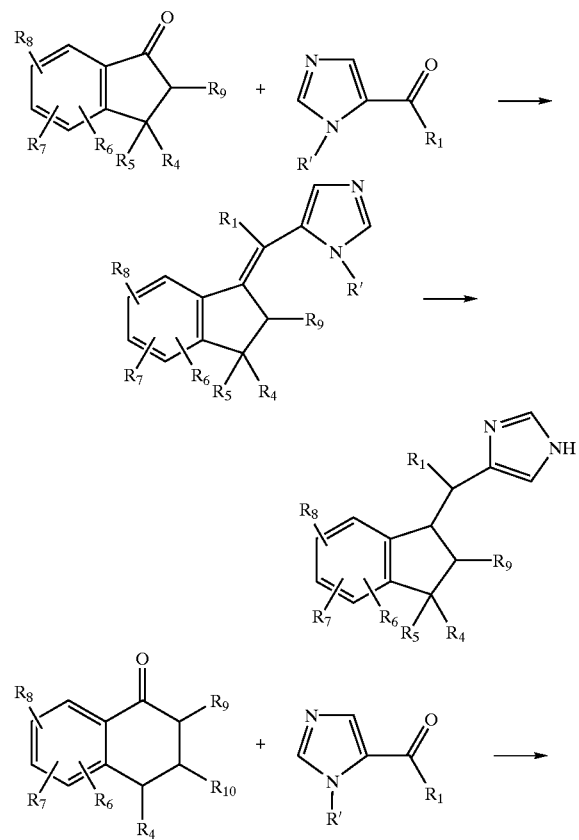

The compounds of the invention may be administered enterally, topically or parenterally. Parenteral administration is used, for example, when the compounds are given as sedative or anxiolytic agents in connection to different clinical operations and to cause analgesia or to potentiate anesthesia.

The compounds of the invention may be formulated alone or together with another active ingredient and/or a pharmaceutically acceptable diluent or carrier to different pharmaceutical unit dosage forms i.e. tablets, capsules, solutions, emulsions and powders etc. using conventional techniques. The pharmaceutical carriers employed are selected with the planned manner of administration in mind. Thus, solid carriers may include lactose, sucrose, gelatin and agar, while liquid carriers typically include waters syrup, peanut oil and olive oil. The amount of the active ingredient varies from 0.01 to 75 weight-% depending on the type of the dosage form.

The appropriate oral dosage for the compounds of the invention depends on several factors such as the compound to be administrated, the species, age and the sex of the subject to be treated, the condition to be treated and on the method of administration. Accordingly, the dosage for parenteral administration is typically from 0.5 $\mu$g/kg to 10 mg/kg per day and that for oral administration is from 5 $\mu$g/kg to 100 mg/kg for an adult male.

The invention also provides a compound of the invention or an ester or salt thereof for use in a method of treatment of human or animal body.

The present invention further provides a compound of the invention or an ester or salt thereof for use in the treatment of hypertension, glaucoma, chronic and acute pain, migraine, diarrhea, common cold, ischemia, addiction to chemical substances, anxiety, especially preoperative anxiety and different neurological, musculoskeletal, psychiatric and cognition disorders or as an adjunct to anesthesia.

The invention also provides the use of a compound of the invention or an ester or salt thereof in the manufacture of a medicament for the treatment of hypertension, glaucoma, chronic and acute pain, migraine, diarrhea, common cold, ischemia, addiction to chemical substances, anxiety, especially preoperative anxiety and different neurological, musculoskeletal, psychiatric and cognition disorders or as an adjunct to anesthesia.

The invention further relates to a method for the treatment of hypertension, glaucoma, chronic and acute pain, migraine, diarrhea, common cold, ischemia, addiction to chemical substances, anxiety, especially preoperative anxiety and different neurological, musculoskeletal, psychiatric and cognition disorders by administering to a subject in need of such treatment an effective amount of the compound of the invention or a pharmaceutically acceptable ester or salt thereof.

Test Results

1. Alpha2 agonism in rat vas deferens model

Alpha2 agonism was determined by means of isolated, electrically stimulated prostatic portions of rat vas deferens preparation (Virtanen et al. Arch. Int. Pharmacodyn et Ther. 297 (1989), pp. 190–204). In this model, an alpha2 agonist is able to inhibit electrically induced muscular contractions by activating the presynaptic alpha2 adrenoceptors and thus diminishing the secretion on the motor transmitter. The known alpha2 agonist dexmedetomidine was used as reference substance. Results are shown in Table 1, where the alpha2 agonist effect is presented as the $pD_2$-value (negative logarithm of the molar concentration of the compound producing 50 percent of maximal inhibition).

The following compounds were tested:

1 4-(4-Methylindan-1-yl)-1H-imidazole hydrochloride
2 3-(1H-Imidazol-4-ylmethyl)-indan-5-ol hydrochloride
3 4-[1-(Indan-1-yl)-ethyl]-1H-imidazole hydrochloride
4 8-(1H-Imidazol-4-ylmethyl)-5,6,7,8-tetrahydronaphthalen-2-ol hydrochloride
5 dexmedetomidine (reference compound)

TABLE 1

Alpha2 agonism in vitro

| Compound | $pD_2$-value |
| --- | --- |
| 1 | 8.1 + −0.2 |
| 2 | 8.5 + −0.1 |
| 3 | 8.9 + −0.3 |
| 4 | 7.0 + −0.1 |
| 5 | 8.4 + −0.1 |

2. Binding assays

Affinities for $\alpha_2$-adrenoceptors and $\alpha_1$-adrenoceptors were estimated by determining the displacement of 1 nM $^3$H-RX821002 ($\alpha_2$) or 0.1 nM $^3$H-prazosin ($\alpha_1$) from α-adrenoceptors in rat neocortical membranes. For this purpose membranes were incubated with different concentrations of test compounds spanning a concentration range of five orders of magnitude. Nonspecific binding was defined with 10 μM phentolamine. Membranes were used at a protein concentration of 2 mg/ml in a total volume of 250 μl. The incubation buffer consisted of 50 mM TRIS-HCl, pH 7.7. After a 30 min incubation at 25° C. samples were filtered through glass fibre filter and filters were washed three times with 4 ml icecold wash buffer consisting of 10 mM TRIS-HCl, pH 7.7. Filters were then dried, impregnated with a scintillation cocktail and counted in a scintillation counter. Experimental data was analyzed using the commercial nonlinear least squares computer program LIGAND.

Each compound was tested in at least three independent experiments for its affinity on rat neocortical $\alpha_2$- or $\alpha_1$-adrenoceptors. The results are shown in Table 2.

TABLE 2

Affinity on rat neocortical $\alpha_2$- or $\alpha_1$-adrenoceptors

| Compound | pKi $\alpha_2$ | pKi $\alpha_1$ | alpha2 vs alpha1 selectivity |
| --- | --- | --- | --- |
| 1 | 8.44 | 7.31 | 14 |
| 2 | 8.70 | 6.61 | 126 |
| 3 | 8.35 | 6.21 | 142 |
| 4 | 7.39 | 6.85 | 3 |
| 5 | 8.42 | 6.48 | 90 |

The following examples illustrate how compounds of the invention may be prepared.

EXAMPLES 4-(6-tert-Butylindan-1-yl)-1H-imidazole a) 3-(4-tert-Butylphenyl)-1-(1H-imidazol-4-yl)-propan-1-ol A solution of 4-tert-butylbenzaldehyde (5.7 g), 1-(3-benzyl-3H-imidazol4-yl)-ethanone (7.0 g) and 48% sodium hydroxide (2.0 ml) in methanol (60 ml) is heated at 60–65° C. for 11 hours. The reaction mixture is then cooled in an ice bath. The resulting precipitate is filtered and the solid intermediate 1-(3-benzyl-3H-imidazol-4-yl)-3-(4-tert-butylphenyl)-propen-1-one is rinsed with methanol. The yield is 10.0 g.

The intermediate is dissolved in the mixture of ethanol (170 ml) and concentrated hydrochloric acid (3 ml). The reaction mixture is hydrogenated at 50–60° C. with 10% palladium on carbon as catalyst until no more hydrogen is consumed. The mixture is filtered and the filtrate is evaporated to dryness. The residue is dissolved in water and is made alkaline with sodium hydroxide. The product is then extracted into methylene chloride which is washed with water, dried with sodium sulfate and evaporated to dryness. The product is converted to its hydrochloride salt in ethyl acetate using dry hydrochloric acid. The yield is 6.8 g.

$^1$H NMR (as HCl-salt, MeOH-$d_4$): 1.29 (s, 9H), 2.06–2.13 (m, 2H), 2.62–2.78 (m, 2H), 4.77 (t, 1H), 7.13 (m, 2H), 7.30 (m, 2H), 7.40 (s, 1H), 8.79 (s, 1H)

b) 4-(6-tert-Butylindan-1-yl)-1H-imidazole

A mixture of 3-(4-tert-butylphenyl)-1-(1H-imidazol4-yl)-propan-1-ol (2.0 g) and methanesulfonic acid (30 ml) is heated at 60° C. for 5 minutes. The reaction is then quenched by pouring it into ice-water solution. The acidic solution is made basic with ammmonium hydroxide solution, and extracted with ethyl acetate. The combined organic layers are washed with water, dried with sodium sulfate, and evaporated to dryness under reduced pressure. The crude product is purified by flash chromatography by eluting with methylene chloride-methanol as eluent. The product is crystallized from ethyl acetate. The yield is 220 mg.

$^1$H NMR (MeOH-$d_4$); 1.24 (s, 9H), 2.07–2.20 (m, 1H), 2.43–2.54 (m, 1H), 2.81–3.01 (m, 2H), 4.35 (t, 1H), 6.74 (s, 1H), 7.09 (s, 1H), 7.14–7.21 (m, 2H), 7.60 (s, 1H)

Using the same method the following compounds were prepared:

4-(Indan-1-yl)-1H-imidazole $^1$H NMR (CDCl$_3$) 2.08–2.19 (m, 1H), 2.41–2.51 (m, 1H), 2.80–2.95 (m, 2H), 4.37 (t, 1H), 6.65 (s, 1H), 7.07–7.21 (m, 4H); 7.25 (s, 1H)

4-(4-Methylindan-1-yl)-1H-imidazole. M.p. of hydrochloride 153–156° C.

$^1$ H NMR (as HCl-salt, MeOH-$d_4$): 2.08–2.20 (m, 1H), 2.30 (s, 3H), 2.58–2.69 (m, 1H), 2.87–3.10 (m, 2H), 4.59 (t, 1H), 6.89 (d, J=7.0 Hz, 1H), 7.05–7.13 (m, 2H), 7.30 (s, 1H), 8.83 (s, 1H)

4-(6-Methylindan-1-yl)-1H-imidazole

¹H NMR (as HCl-salt, MeOH-d₄): 2.07–2.20 (m, 1H), 2.28 (s, 3H), 2.55–2.66 (m, 1H), 2.89–3.08 (m, 2H), 4.53 (t, 1H), 6.88 (s, 1H), 7.06 (d, J=7.8 Hz, 1H), 7.19 (d, J=7.8 Hz, 1H), 7.30 (s, 1H), 8.79 (s, 1H)

4-(6-Ethylindan-1-yl)-1H-imidazole

¹H NMR (as HCl-salt, MeOH-d₄): 1.17 (t, 3H), 2.08–2.21 (m, 1H), 2.55–2.67 (m, 3H), 2.90–3.10 (m, 2H), 4.56 (t, 1H), 6.91 (s, 1H), 7.08 (d, J=7.7 Hz, 1H), 7.22 (d, J=7.7 Hz, 1H), 7.32 (s, 1H), 8.85 (s, 1H)

4-(4,5-Dimethylindan-1-yl)-1H-imidazole. M.p of hydrochloride 161–164° C.

¹H NMR (as HCl-salt, MeOH-d₄) 2.06–2.18 (m, 1H), 2.22 (s, 3H), 2.26 (s, 3H), 2.56–2.68 (m, 1H), 2.87–3.11 (m, 2H), 4.55 (t, 1H), 6.78 (d, J=7.6 Hz, 1H), 6.99 (d, J=7.6 Hz, 1H), 7.27 (s, 1H), 8.80 (s, 1H)

4-(5,7-Dimethylindan-1-yl)-1H-imidazole

¹H NMR (CDCl₃); 2.07 (s, 3H), 2.07–2.22 (m, 1H), 2.31 (s, 3H), 2.40–2.53 (m, 1H), 2.77–2.87 (m, 1H), 2.94–3.05 (m, 1H), 4.44 (m, 1H), 6.55 (s, 1H), 6.80 (s, 1H), 6.94 (s, 1H), 7.53 (s, 1H)

4-(2,4-Dimethylindan-1-yl)-1H-imidazole

¹H NMR (CDCl₃): 1.23 (d, 3H), 2.28 (s, 3H), 2.46–2.55 (m, 2H), 3.05–3.16 (m, 1H), 3.92 (d, 1H), 6.81–6.83 (m, 2H), 6.95–7.09 (m, 2H), 7.56 (s, 1H)

4-(5-Methoxyindan-1-yl)-1H-imidazole. M.p. 180–184° C.

¹H NMR (CDCl₃+MeOH-d₄); 2.09–2.19 (m, 1H), 2.48–2.59 (m, 1H), 2.87–2.98 (m, 2H), 3.79 (s, 3H), 4.35 (t, 1H), 6.69–6.73 (m, 2H), 6.82 (d, J=2.0 Hz, 1H), 7.03 (d, J=8.2 Hz, 1H), 7.53 (s, 1H)

4-(7-Methoxyindan-1-yl)-1H-imidazole

¹H NMR (CDCl₃); 2.20–2.50 (m, 2H), 2.83–2.98 (m, 2H), 3.82 (s, 3H), 4.50–4.54 (m, 1H), 6.66–6.72 (m, 2H), 6.86 (d, J=7.7 Hz, 1H), 7.16 (t, J=7.7 Hz, 1H), 7.43 (s, 1H)

EXAMPLE 2

4-(1-Methylindan-1-yl)-1H-imidazole a) 2-(3-Benzyl-3H-imidazol-4-yl)4-phenylbutan-2-ol 1.0 g of magnesium turnings are covered with 5 ml of dry tetrahydrofuran. To the mixture is added 7.8 g of (2-bromoethyl)benzene in 30 ml of dry tetrahydrofuran at such a rate that a smooth reaction is maintained. The mixture is then heated under reflux for one hour. After being cooled to room temperature, 3.0 g of 1-(3-benzyl-3H-imidazol-4-yl)-ethanone in 20 ml of tetrahyrofuran is added dropwise to the Grignard reagent and the reaction mixture is refluxed for one hour. The cooled reaction mixture is poured into a cold dilute hydrochloric acid solution. Work-up of the mixture gives the crude product, which is recrystallized from ethyl acetate. The yield is 3.3 g.

¹H NMR (as HCl-salt, MeOH-d₄): 1.67 (s, 3H), 2.01–2.08 (m, 2H), 2.37–2.48 (m, 1H), 2.57–2.71 (m, 1H), 5.75 (dd, 2H), 6.97–7.42 (m, 10H), 7.50 (s, 1H), 8.75 (s, 1H)

b) 2-(1H-Imidazol-4-yl)4-phenylbutan-2-ol 3.3 g of 2-(3-benzyl-3H-imidazol-4-yl)-4-phenylbutan-2-ol is dissolved in 100 ml of ethanol. The reaction solution is hydrogenated at 50° C. with 10% palladium on carbon as catalyst for 4.5 hours. Work-up of the reaction mixture gives the crude product, which is recrystallized from ethyl acetate. The yield is 2.0 g.

¹H NMR (MeOH-d₄): 1.56 (s, 3H), 2.01–2.13 (m, 2H), 2.37–2.47 (m, 1H), 2.53–2.64 (m, 1H), 6.96 (s, 1H), 7.07–7.13 (m, 3H), 7.18–7.23 (m, 2H), 7.61 (s, 1H)

c) 4-(1-Methylindan-1-yl)-1H-imidazole

A mixture of 2-(1H-imidazol-2-yl)-4-phenylbutan-2-ol (0.5 g) and methanesulfonic acid (12 ml) is heated at 100° C. for 35 minutes. The cooled reaction mixture is poured into water and is made alkaline with sodium hydroxide solution. The product is extracted into ethyl acetate which is washed with water, dried with sodium sulfate and evaporated under reduced pressure. The product is converted to its hydrochloride salt in ethyl acetate using dry hydrochloric acid. The yield is 387 mg, m.p. 164–171° C.

¹H NMR (as HCl-salt, MeOH-d₄): 1.67 (s, 3H), 2.21–2.30 (m, 1H), 2.40–2.50 (m, 1H), 2.96–3.11 (m, 2H), 7.06–7.33 (m, 5H), 8.84 (s, 1H)

EXAMPLE 3

4-(5-Chloro-1,2,3,4-tetrahydronaphthalen-1-yl)-1H-imidazole a) 4-(2-Chlorophenyl)-1-(1H-imidazol-4-yl)-butan-1-ol 3.3 g of magnesium turnings are covered with 40 ml of dry tetrahydrofuran. To the mixture is added 32.0 g of 1-(3-bromopropyl)-2-chlorobenzene (prepared according to Baddar, F. G. et al., J. Chem. Soc., 1959, 1027) in 100 ml of dry tetrahydrofuran at such a rate that a smooth reaction is maintained. When the magnesium turnings have reacted the solution is cooled to room temperature. 4.3 g of imidazole-4-carbaldehyde in 40 ml of dry tetrahydrofuran is then added dropwise to the Grignard reagent and the reaction mixture is refluxed for one hour. The cooled reaction mixture is poured into a cold dilute hydrochloric acid solution. Tetrahydrofuran is distilled off under reduced pressure and the residue is cooled. The resulting precipitate is filtered and washed with water. The crude product is recrystallized from ethanol. The yield is 8.0 g. Melting point of the hydrochloride salt is 152–154° C.

¹H NMR (as HCl-salt, MeOH-d₄): 1.65–1.91 (m, 4H), 2.80 (t, 2H), 4.82, (t, 1H), 7.14–7.35 (m, 4H), 7.40 (s, 1H), 8.83 (s, 1H)

b) 4-(5-Chloro-1,2,3,4-tetrahydronaphthalen-1-yl)-1H-imidazole

A mixture of 4-(2-chlorophenyl)-1-(1H-imidazol-4-yl)-butan-1-ol hydrochloride (1.0 g) and methanesulfonic acid (15 ml) is heated at 100° C. for 2 hours. The cooled reaction mixture is poured into water and is made alkaline with sodium hydroxide solution. The product is extracted into ethyl acetate which is washed with water, dried with sodium sulfate and evaporated under reduced pressure. The crude product is recrystallized from ethyl acetate. The yield is 0.4 g, m.p. 165–169° C.

¹H NMR (CDCl₃): 1.74–1.83 (m, 2H), 1.95–2.15 (m, 2H), 2.70–2.91 (m, 2H), 4.19 (t, 1H), 6.49 (s, 1H), 6.96–7.05 (m, 2H), 7.21–7.24 (m, 1H), 7.54 (s, 1H)

EXAMPLE 4

4-(1,2,3,4-Tetrahydronaphthalen-1-yl)-1H-imidazole 4-(5-Chloro-1,2,3,4-tetrahydronaphthalen-1-yl)-1H-imidazole (300 mg) is dissolved in ethanol (15 ml). The reaction solution is hydrogenated at 50° C. with 10% palladium on carbon as catalyst for 8 hours. The mixture is filtered to remove the catalyst, and the filtrate is evaporated under reduced pressure. The residue is dissolved in water and is made alkaline with sodium hydroxide solution. The product is extracted into methylene chloride which is washed with water, dried with sodium sulfate and evaporated under reduced pressure. The crude product is recrystallized from ethyl acetate. The yield is 169 mg, m.p. 105–110° C.

¹H NMR (CDCl₃): 1.70–1.85 (m, 2H), 2.05–2.11 (m, 2H), 2.78–2.86 (m, 2H), 4.21 (t, 1H), 6.59 (s, 1H), 7.04–7.14 (m, 4H), 7.52 (s, 1H)

EXAMPLE 5
3-(1H-Imidazol4-yl)-5-isobutylindan-1-ol a) 3-(3-Benzyl-3H-imidazol-4-yl)-1-(4-isobutylphenyl)-propen-1-one A solution of 4-isobutylacetophenone (2.0 g), 3-benzyl-3H-imidazole-4-carbaldehyde (2.1 g) and 48% sodium hydroxide (0.65 ml) in methanol (20 ml) is heated at 55–60° C. for 6 hours. The reaction mixture is then cooled in an ice bath. The resulting precipitate is filtered, and rinsed with methanol. The yield is 2.5 g.

$^1$H NMR (CDCl$_3$): 0.91 (d, 6H), 1.85–1.95 (m, 1H), 2.54 (d, 2H), 5.28 (s, 2H), 7.12–7.14 (m, 2H), 7.23 (d, J=8.2 Hz, 2H), 7.30–7.41 (m, 4H), 7.60–7.68 (m, 3H), 7.80 (d, J=8.2 Hz, 2H)

b) 3-(3-Benzyl-3H-imidazol-4-yl)-5-isobutylindan-1-one

A mixture of 3-(3-benzyl-3H-imidazol-4-yl)-1-(4-isobutylphenyl)-propen-1-one (2.4 g) and methanesulfonic acid (40 ml) is heated at 120° C. for 40 minutes. Work-up of the reaction mixture gives the crude product, which is purified by flash chromatography by eluting with methylene chloride-methanol solution. The yield is 0.5 g.

$^1$H NMR (CDCl$_3$): 0.89 (d, 6H), 1.81–1.91 (m, 1H), 2.34 (dd, J=18.8 Hz, J=4.0 Hz, 1H), 2.51 (d, 2H), 2.80 (dd, J=18.8 Hz, J=7.9 Hz, 1H), 4.44–4.48 (m, 1H), 5.03–5.16 (m, 2H), 6.64 (s, 1H), 7.05–7.08 (m, 2H), 7.13 (s, 1H), 7.22 (d, J=7.8 Hz, 1H), 7.26–7.39 (m, 3H), 7.57 (s, 1H), 7.68 (d, J=7.8 Hz, 1H)

c) 3-(1H-Imidazol-4-yl)-5-isobutylindan-1-ol 3-(3-Benzyl-3H-imidazol-4-yl)-5-isobutylindan-1-one (0.5 g) is dissolved in ethanol (15 ml). The reaction solution is hydrogenated at 50° C. with 10% palladium on carbon as catalyst until no more hydrogen is consumed. The mixture is filtered to remove the catalyst, and the filtrate is evaporated under reduced pressure. The crude product contains cis- and trans-isomers. The isomers are purified by flash chromatography.

$^1$H NMR (cis-isomer, CDCl$_3$): 0.85 (d, 6H), 1.74–1.84(m, 1H), 2.15–2.20 (m, 1H), 2.40 (d, 2H), 2.69–2.79 (m, 1H), 4.33 (d, 1H), 5.16 (d, 1H), 6.91 (s, 1H), 6.93 (s, 1H), 7.02 (d, J=7.7 Hz, 1H), 7.39 (d, J=7.7 Hz, 1H), 7.42 (s, 1H) $^1$H NMR (trans-isomer, CDCl$_3$): 0.85 (d, 6H), 1.74–1.84 (m, 1H), 2.35–2.46 (m, 4H), 4.60 (t, 1H), 5.26 (t, $_1$H), 6.65 (s, 1H), 6.95 (s, 1H), 7.04 (d, J=7.7 Hz, 1H), 7.33 (d, J=7.7 Hz, 1H), 7.46 (s, 1H)

EXAMPLE 6
3-(1H-Imidazol-4-yl)-5-methoxy-6,7-dimethylindan-1-one a) 3-(3-Benzyl-3H-imidazol-4-yl)-5-methoxy-6,7-dimethylindan-1-one A mixture of 2,3-dimethylanisole (2.0 g), 3-(3-benzyl-3H-imidazol-4-yl)-acrylic acid (3.4 g) and methanesulfonic acid (60 ml) is heated at 90–95° C. for 45 minutes. The cooled reaction mixture is poured into water and is made alkaline with sodium hydroxide solution. The product is extracted into ethyl acetate which is washed with water, dried with sodium sulfate and evaporated in reduced pressure. The crude product is purified by flash chromatography by eluting with methylene chloride-methanol solution. The yield is 1.1 g.

$^1$H NMR (CDCl$_3$): 2.13 (s, 3H), 2.35 (dd, J=18.5 Hz, J=4.1 Hz, 1H), 2.61 (s, 3H), 2.81 (dd, J=18.5 Hz, J=8.2 Hz, 1H), 3.76 (s, 3H), 4.34–4.38 (m, 1H), 5.05 (s, 2H), 6.52 (s, 1H), 6.72 (s, 1H), 7.00–7.05 (m, 2H), 7.29–7.36 (m, 3H), 7.56 (s, 1H)

b) 3-(1H-Imidazol-4-yl)-5-methoxy-6,7-dimethylindan-1-one 3-(3-Benzyl-3H-imidazol-4-yl)-5-methoxy-6,7-dimethylindan-1-one (1.1 g) is dissolved in ethanol (90 ml). The reaction solution is hydrogenated at 50–55° C. with 10% palladium on carbon as catalyst for 7 hours. The mixture is filtered to remove the catalyst, and the filtrate is evaporated under reduced pressure. The product is converted to its hydrochloride salt in ethyl acetate using dry hydrochloric acid. The yield is 0.6 g, m.p. 258–261° C.

$^1$H NMR (as HCl-salt, MeOH-d$_4$): 2.16 (s, 3H), 2.62 (s, 3H), 2.68 (dd, J=18.7 Hz, J=4.0 Hz, 1H), 3.18 (dd, J=18.7 Hz, J=8.3 Hz, 1H), 3.87 (s, 3H), 4.77–4.81 (m, 1H), 6.81 (s, 1H), 7.43 (s, 1H), 8.85 (s, 1H)

Using the same method the following compound was prepared:

3-(1H-Imidazol-4-yl)-5-methoxy-4,7-dimethylindan-1-one $^1$H NMR (CDCl$_3$): 1.96 (s, 3H), 2.64 (dd, J=18.6 Hz, J=2.1 Hz, 1H), 2.65 (s, 3H), 3.13 (dd, J=18.6 Hz, J=8.4 Hz, 1H), 3.90 (s, 3H), 4.57–4.61 (m, 1H), 6.47 (s, 1H), 6.68 (s, 1H), 7.50 (s, 1H)

EXAMPLE 7
3-(1H-Imidazol-4-yl)-5-methoxy-6,7-dimethylindan-1-ol 3-(1H-Imidazol-4-yl)-5-methoxy-6,7-dimethylindan-1-one (0.53 g) is dissolved in ethanol (30 ml) and 0.3 g of sodium borohydride is added. The mixture is stirred at 35–40° C. for 7 hours. About 20 ml of ethanol is then distilled off and 30 ml of water is added. The solution is extracted with ethyl acetate. The combined ethyl acetate extracts are washed with water, dried with sodium sulfate, and evaporated under reduced pressure. The product is the mixture of cis- and trans-isomers (about 85:15). Crystallization of the product from ethyl acetate gives a cis-isomer, m.p. 184–189° C.

$^1$H NMR (cis-isomer, CDCl$_3$): 2.09–2.14 (m, 1H), 2.11 (s, 3H), 2.38 (s, 3H), 2.69–2.77 (m, 1H), 3.73 (s, 3H), 4.31 (d, 1H), 5.26 (d, 1H), 6.48 (s, 1H), 6.90 (s, 1H), 7.43 (s, 1H)

EXAMPLE 8
4-(6-Methoxy-4,5-dimethylindan-1-yl)-1H-imidazole 3-(1H-Imidazol-4-yl)-5-methoxy-6,7-dimethylindan-1-ol (0.29 g) is dissolved in the mixture of ethanol (30 ml) and concentrated hydrochloric acid (0.2 ml). The solution is hydrogenated at 50–55° C. with 10% palladium on carbon as catalyst until no more hydrogen is consumed. The mixture is filtered and the filtrate is evaporated to dryness. The residue is crystallized from the mixture of ethyl acetate and ethanol. M.p. of the hydrochloride salt is 174–177° C.

$^1$H NMR (as HCl-salt, MeOH-d$_4$): 2.05–2.17 (m, 1H), 2.11 (s, 3H), 2.21 (s, 3H), 2.54–2.66 (m, 1H), 2.82–3.05 (m, 2H), 3.71 (s, 3H), 4.55 (t, 1H), 6.50 (s, 1H), 7.27 (s, 1H), 8.79 (s, 1H)

Using the same method the following compound was prepared:

4-(6-Isobutylindan-1-yl)-1H-imidazole $^1$H NMR (as HCl-salt, MeOH-d$_4$): 0.86 (d, 6H), 1.73–1.83 (m, 1H), 2.11–2.18 (m, 1H), 2.42 (d, 2H), 2.58–2.65 (m, 1H), 2.97–3.31 (m, 2H), 4.56 (t, 1H), 6.85 (s, 1H), 7.04 (d, J=7.6 Hz, 1H), 7.22 (d, J=7.6 Hz, 1H), 7.30 (s, 1H), 8.83 (s, 1H)

EXAMPLE 9
3-(1H-imidazol-4-yl)-6,7-dimethylindan-5-ol

A stirred mixture of 4-(6-methoxy-4,5-dimethylindan-1-yl)-1H-imidazole hydrochloride (0.29 g) and hydrobromic acid (15 ml) is heated under reflux for 40 minutes. The cooled reaction mixture is poured into water and is made basic with ammonium hydroxide solution. The product is extracted into ethyl acetate which is washed with water, dried with sodium sulfate and evaporated to dryness. The crude product is purified by flash chromatography and crystallized from ethyl acetate. M.p. 198–202° C.

$^1$H NMR (CDCl$_3$+MeOH-d$_4$): 2.02–2.13 (m, 1H), 2.13 (s, 3H), 2.18 (s, 3H), 2.43–2.54 (m, 1H), 2.71–2.82 (m, 1H), 2.86–2.96 (m, 1H), 4.33 (t, 1H), 6.49 (s, 1H), 6.75 (s, 1H), 7.50 (s, 1H)

Using the same method the following compound was prepared:

5-Hydroxy-3-(1H-imidazol-4-yl)-6,7-dimethylindan-1-one $^1$H NMR (MeOH-d$_4$): 2.12 (s, 3H), 2.58 (s, 3H), 2.67 (dd, J=18.4 Hz, J=4.1 Hz, 1H), 3.02 (dd, J=18.4 Hz, J=8.0 Hz, 1H), 4.43–4.47 (m, 1H), 6.59 (s, 1H), 6.90 (s, 1H), 7.62 (s, 1H)

1-(1H-Imidazol-4-yl)-indan5-ol. M.p. 210–220° C.

$^1$H NMR(MeOH-d$_4$): 2.04–2.17 (m, 1H), 2.41–2.52(m, 1H), 2.77–2.97 (m, 2H), 4.27 (t, 1H), 6.55 (dd, J=8.1 Hz, J=2.3 Hz, 1H), 6.67 (d, J=2.3 Hz, 1H), 6.70 (s, 1H), 6.84 (d, J=8.1 Hz, 1H), 7.57 (s, 1H)

3-(1H-imidazol-4-yl)-indan-4-ol. M.p. 142–145° C.

$^1$H NMR (CDCl$_3$+MeOH-d$_4$): 2.13–2.26 (m, 1H), 2.49–2.60 (m, 1H). 2.89–3.08 (m, 2H), 4.54 (t, 1H), 6.71–6.76 (m, 3H), 7.06 (t, J=7.6 Hz, 1H), 7.55 (s, 1H)

EXAMPLE 10

4-(3-Ethoxy-6-methoxy4,5-dimethylindan-1-yl)-1H-imidazole (cis-isomer)

3-(1H-Imidazol4-yl)-5-methoxy-6,7-dimethylindan-1-ol (cis-isomer, 0.1 g) is dissolved in the mixture of ethanol (20 ml) and concentrated hydrochloric acid (2 ml). The solution is stirred at 25° C. for one hour. Work-up of the reaction mixture gives the crude product, which is purified by flash chromatography using methylene chloride-methanol as eluent.

$^1$H NMR (CDCl$_3$): 1.31 (t, J=7.0 Hz, 3H), 2.12 (s, 3H), 2.20–2.25 (m, 1H), 2.32 (s, 3H), 2.51–2.60 (m, 1H), 3.72 (q, J=7.0 Hz, 2H), 3.73 (s, 3H), 4.40 (d, 1H), 4.96 (d, 1H), 6.52 (s, 1H), 6.93 (s, 1H), 7.41 (s, 1H)

EXAMPLE 11

4-(Indan-1-yl)-1H-imidazole a) 4-(3H-Inden-1-yl)-1H-imidazole

To a stirred solution of 1-(N,N-dimethylsulfamoyl)-1H-imidazole (1.9 g, prepared according to Chadwick, D. J. and Ngochindo, R. I., J. Chem. Soc., Perkin Trans. (1984, 481) in dry tetrahydrofuran (90 ml) at −70° C. under nitrogen, is added dropwise 2.5 M butyllithium in hexane (5.1 ml). After 30 minutes tert-butyldimethylsilyl chloride (2.0 g) in dry tetrahydrofuran (5 ml) is added and the mixture is allowed to warm to 25° C. After 1.5 hours the mixture is again cooled to −70° C. and treated with 2.5 M butyllithium in hexane (5.3 ml). After 30 minutes, 1-indanone (2.1 g) in dry tetrahydrofuran (5 ml) is added and the mixture is allowed to warm to room temperature. The reaction mixture is then quenched with saturated Na$_2$CO$_3$ solution (2 ml), and the solvent is removed under reduced pressure. The residue is dissolved in methylene chloride and washed with water, dried with sodium sufate and evaporated to dryness under reduced pressure. The bis-protected intermediate is refluxed with 2 N hydrochloric acid (200 ml) for 2 hours. The cooled solution is made basic by ammonium hydroxide solution, and extracted with methylene chloride. The organic layer is washed with water, dried with sodium sulfate and the solvent removed under reduced pressure. The crude product is purified by flash chromatography using methylene chloride-methanol as eluent. The product is converted to the hydrochloride salt in ethyl acetate-ethanol solution, m.p. 232–240° C.

$^1$H NMR (as HCl-salt, MeOH-d$_4$); 3.66 (d, 2H), 7.07 (t, 1H), 7.31–7.43 (m, 2H), 7.59 (d, 1H), 7.68 (d, 1H), 8.03 (s, 1H), 9.06 (s, 1H)

b) 4-(Indan-1-yl)-1H-imidazole 4-(3H-Inden-1-yl)-1H-imidazole hydrochloride (80 mg) is dissolved in ethanol (6 ml). The reaction solution is hydrogenated at 40–50° C. with 10% palladium on carbon as catalyst until no more hydrogen is consumed. Work-up of the reaction mixture gives the crude product which is purified by flash chromatography using methylene chloride-methanol as eluent.

$^1$H NMR (CDCl$_3$): 2.08–2.19 (m, 1H), 2.41–2.51 (m, 1H), 2.80–2.95 (m, 2H), 4.37 (t, 1H), 6.65 (s, 1H), 7.07–7.21 (m, 4H), 7.25 (s, 1H)

Using the same method the following compound was prepared:

4-(6-Methoxyindan-1-yl)-1H-imidazole $^1$H NMR (as HCl-salt, MeOH-d$_4$): 2.08–2.20 (m, 1H), 2.56–2.67 (m, 1H), 2.80–2.97 (m, 2H), 3.72 (s, 3H), 4.53 (t, 1H), 6.71 (d, J=1.9 Hz, 1H), 6.75 (dd, J=8.3 Hz, J=1.9 Hz, 1H), 6.92 (s, 1H), 7.15 (d, J=83 Hz, 1H), 8.82 (s, 1H)

EXAMPLE 12

4-(Indan-1-ylmethyl)-1H-imidazole

Titanium tetrachloride (17.2 g) is added dropwise to a stirred suspension of zinc powder (11.9 g) in tetrahydrofuran (100 ml) with ice cooling under a nitrogen atmosphere. The mixture is heated at reflux for one hour. After being cooled to room temperature, 1-indanone (2.0 g) and 3-benzyl-3H-imidazole-4-carbaldehyde (4.2 g) in tetrahydrofuran (30 ml) are added into the mixture. The mixture is refluxed with stirring for 3 hours. The cooled reaction mixture is made alkaline with dilute sodium hydroxide solution. The slurry is filtered, and the filtratate is evaporated to dryness under reduced pressure. The residue, which contains the crude intermediate 1-benzyl-5-(indan-1-ylidenemethyl)-1H-imidazole is purified by flash chromatography.

The purified intermediate (0.8 g) is dissolved in the mixture of ethanol (30 ml), water (2 ml) and concentrated hydrochloric acid (0.5 ml). The reaction mixture is hydrogenated at 50–60° C. with 10% palladium on carbon as catalyst until no more hydrogen is consumed. The mixture is filtered, and the filtrate is evaporated to dryness. The residue is dissolved in water and is made alkaline with sodium hydroxide. The product is then extracted into methylene chloride which is washed with water, dried with sodium sulfate and evaporated to dryness. The product is converted to its hydrochloride salt in ethyl acetate using dry hydrochloric acid. The yield is 0.5 g, m.p. 182–183° C.

$^1$H NMR (as HCl-salt, MeOH-d$_4$): 1.74–1.81 (m, 1H), 2.22–2.29 (m, 1H), 2.80–2.95 (m, 3H), 3.17 (dd, J=15.1 Hz, J=5.7 Hz, 1H), 3.48–3.53 (m, 1H), 7.12–7.23 (m, 4H), 7.26 (s, 1H), 8.79 (s, 1H).

Using the same method the following compounds were prepared:

4-(6-Methoxyindan-1-ylmethyl)-1H-imidazole. M.p. of hydrochloride 197–200° C.

$^1$H NMR (as HCl-salt, MeOH-d$_4$): 1.72–1.84 (m, 1H), 2.19–2.31 (m, 1H), 2.70–2.89 (m, 3H), 3.16 (dd, J=14.9 Hz, J=5.5 Hz, 1H), 3.42–3.51 (m, 1H), 3.74 (s, 3H), 6.68 (d, J=2.2 Hz, 1H), 6.74 (dd, J=8.2 Hz, J=2.2 Hz, 1H), 7.10 (d, J=8.2 Hz, 1H), 7.27 (s, 1H), 8.82 (s, 1H)

4-(5-Methoxyindan-1-ylmethyl)-1H-imidazole. M.p. of hydrochloride 204–206° C.

$^1$H NMR (as HCl-salt, MeOH-d$_4$): 1.71–1.83 (m, 1H), 2.19–2.31 (m, 1H), 2.75–2.94 (m, 3H), 3.13 (dd, J=15.0 Hz, J=5.5 Hz, 1H), 3.40–3.49 (m, 1H), 3.75 (s, 3H), 6.70 (dd, J=8.3 Hz, J=2.2 Hz, 1H), 6.78 (d, J=2.2 Hz, 1H), 7.00 (d, J=8.3 Hz, 1H), 7.26 (s, 1H), 8.82 (s, 1H)

4-(5,6-Dimethoxyindan-1-ylmethyl)-1H-imidazole. M.p. of hydrochloride 193–197° C.

$^1$H NMR (as HCl-salt, MeOH-d$_4$): 1.72–1.84 (m, 1H), 2.20–2.32 (m, 1H), 2.75–2.88 (m, 3H), 3.15 (dd, J=15.1 Hz, J=5.2 Hz, 1H), 3.41–3.50 (m, 1H), 3.77 (s, 3H), 3.79 (s, 3H), 6.73 (s, 1H), 6.84 (s, 1H), 7.26 (s, 1H), 8.82 (s, 1H)

4-(6-Methoxy-4,5-dimethylindan-1-ylmethyl)-1H-imidazole. M.p. of hydrochloride 194–197° C.

$^1$H NMR (as HCl-salt, MeOH-d$_4$): 1.70–1.81 (m, 1H), 2.09 (s, 3H), 2.15 (s, 3H), 2.17–2.29 (m, 1H), 2.69–2.89 (m, 3H), 3.14 (dd, J=15.1 Hz, J=5.7 Hz, 1H), 3.42–3.50 (m, 1H), 3.74 (s, 3H), 6.54 (s, 1H), 7.24 (s, 1H), 8.81 (s, 1H)

4-(6-Methoxy-4,7-dimethylindan-1-ylmethyl)-1H-imidazole. M.p. of hydrochloride 168–175° C.

$^1$H NMR (as HCl-salt, MeOH-d$_4$); 1.88–1.94 (m, 1H), 2.07 (s, 3H), 2.09–2.18 (m, 1H), 2.19 (s, 3H), 2.69–2.77 (m, 3H), 2.90 (dd, J=15.2 Hz, J=4.7 Hz, 1H), 3.51–3.57 (m, 1H), 3.77 (s, 3H), 6.60 (s, 1H), 7.21 (s, 1H), 8.80 (s, 1H)

4-(6-Methoxy-5-methylindan-1-ylmethyl)-1H-imidazole. M.p. of hydrochloride 183–186° C.

$^1$H NMR (as HCl-salt, MeOH-d$_4$): 1.71–1.82 (m, 1H), 2.13 (s, 3H), 2.18–2.29 (m, 1H), 2.70–2.89 (m, 3H), 3.16 (dd, J=15.0 Hz, J=5.4 Hz, 1H), 3.42–3.50 (m, 1H), 3.76 (s, 3H), 6.65 (s, 1H), 6.95 (s, 1H), (s, 1H), 8.82 (s, 1H)

4-(6-Fluoroindan-1-ylmethyl)-1H-imidazole. M.p. of hydrochloride 215–222° C.

$^1$H NMR (as HCl-salt, MeOH-d$_4$): 1.76–1.88 (m, 1H), 2.23–2.35 (m, 1H), 2.76–2.92 (m, 3H), 3.18 (dd, J=15.3 Hz, J=5.3 Hz, 1H), 3.46–3.56 (m, 1H), 6.86–6.92 (m, 2H), 7.17–7.20 (m, 1H), 7.31 (s, 1H), 8.83 (s, 1H)

4-(5-Fluoroindan-1-ylmethy)-1H-imidazole. M.p. of hydrochloride 185–189° C.

$^1$H NMR (as HCl-salt, MeOH-d$_4$): 1.76–1.88 (m, 1H), 2.23–2.35 (m, 1H), 2.79–2.98 (m, 3H), 3.16 (dd, J=15.3 Hz, J=5.3 Hz, 1H), 3.43–3.53 (m, 1H), 6.83–6.96 (m, 2H), 7.08–7.13 (m, 1H), 7.29 (s, 1H), 8.82 (s, 1H)

4-(4-Methoxyindan-1-ylmethyl)-1H-imidazole. M.p. of hydrochloride 202–210° C.

$^1$H-NMR (as HCl-salt, MeOH-d$_4$): 1.73–1.82 (m, 1H), 2.18–2.30 (m, 1H), 2.72–289 (m, 3H), 3.14 (dd, J=15.0 Hz, J=5.5 Hz, 1H), 3.48–3.56 (m, 1H), 3.80 (s, 3H), 6.72–6.78 (m, 2H), 7.14 (t, 1H), 7.24 (s, 1H), 8.79 (s, 1H)

4-(6-Methoxy-7-methylindan-1-ylmethyl)-1H-imidazole. M.p. of hydrochloride 152–158° C.

$^1$NMR (as HCl-salt, MeOH-d$_4$): 1.86–1.93 (m, 1H), 2.11 (s, 3H), 2.12–2.20 (m, 1H), 2.68–2.96 (m, 4H), 3.52–3.59 (m, 1H), 3.79 (s, 3H), 6.75 (d, J=8.2 Hz, 1H), 6.99 (d, J=8.2 Hz, 1H), 7.22 (s, 1H), 8.79 (s, 1H)

EXAMPLE 13
4-[1-(Indan-1-yl)-ethyl]-1H-imidazole

The procedure of Example 12 is repeated except that 1-(3-benzyl-3H-imidazol-4-yl)-ethanone is used in place of 3-benzyl-3H-imidazole-4-carbaldehyde. The product contains two diastereomers ad and bc (78% of ad and 22% of bc).

$^1$H NMR (as HCl-salt, MeOH-d$_4$): 1.23 (d, J=7.1 Hz, —CH$_3$, bc diastereomer), 1.38 (d, J=7.1 Hz, —CH$_3$, ad diastereomer), 1.81–2.32 (m, 2H), 2.70–2.87 (m, 2H), 3.29–3.39 (m, 1H), 3.47–3.57 (m, 1H), 6.98–7.30 (m, 5H), 8.77 (s, 1H, ad (diastereomer), 8.84 (s, 1H, bc diastereomer)

Using the same method the following substituted derivative was prepared:

4-[1-(6-Methoxyindan-1-yl)-ethyl]-1H-imidazole

The reaction mixture contains two diastereomers ad and bc, which are separated by flash chromatography eluting with methylene chloride-methanol solution.

$^1$H NMR (ad diastereomer as HCl-salt, MeOH-d$_4$): 1.37 (d, J=7.1 Hz, 3H), 1.83–1.94 (m, 1H), 2.20–2.33 (m, 1H), 2.58–2.77 (m, 2H), 3.30–3.39 (m, 1H), 3.43–3.49 (m, 1H), 3.74 (s, 3H), 6.63 (d, J=2.4 Hz, 1H), 6.73 (dd, J=8.2 Hz, J=2.4 Hz, 1H), 7.05 (d, J=8.2 Hz, 1H), 7.13 (s, 1H), 8.74 (s, 1H)

$^1$H NMR (bc diastereomer as HCl-salt, MeOH-d$_4$): 1.23 (d, J=7.1 Hz, 3H), 1.90–2.01 (m, 1H), 2.05–2.16 (m, 1H), 2.70–81 (m, 2H), 3.29–3.39 (m, 1H), 3.43–3.54 (m, 1H), 3.72 (s, 3H), 6.54 (d, J=2.4 Hz, 1H) 6.73 (dd, J=8.2 Hz, J2.4 Hz, 1H) 7.11 (d, J=8.2 Hz, 1H), 7.32 (s, 1H), 8.84 (s, 1H)

EXAMPLE 14
4-(5-tert-Butyl-6-methoxyindan-1-ylmethyl)-1H-imidazole

Sulfuric acid (0.5 ml) is added into the mixture of 4-(6-methoxyindan-1-ylmethyl)-1H-imidazole hydrochloride (50 mg) and tert-butanol (2 ml). The mixture is stirred at 35–40° C. for 10 hours. The reaction mixture is then poured into water and is made alkaline with sodium hydroxide. The product is extracted into methylene chloride which is washed with water, dried with sodium sulfate and evaporated to dryness. The residue consisting of crude product is converted to its hydrochloride salt in ethyl acetate. The yield is 23 mg, m.p. 174–184° C.

$^1$H NMR (as HCl-salt, MeOH-d$_4$): 1.33 (s, 9H), 1.71–1.83 (m, 1H), 2.19–2.31 (m, 1H), 2.73–2.89 (m, 3H), 3.15 (dd, J=15.0 Hz, J=5.1 Hz, 1H), 3.40–3.50 (m. 1H), 3.77 (s, 3 H), 6.69 (s, 1H), 7.11 (s, 1H), 7.27 (s, 1H), 8.81 (s, 1H)

Using the same method the following compound was prepared:

4-(6-tert-Butyl-5-methoxyindan-1-ylmethyl)-1H-imidazole $^1$H NMR (as HCl-salt, MeOH-d$_4$): 1.30 (s, 9H), 1.73–1.84 (m, 1H), 2.21–2.33 (m, 1H), 2.75–2.94 (m, 3H), 3.05 (dd, J=14.9 Hz, J=6.3 Hz, 1H), 3.35–3.45 (m, 1H), 3.80 (s, 3H), 6.83 (s, 1H), 6.86 (s, 1H), 7.23 (s, 1H), 8.81 (s, 1H)

5,7-Di-tert-butyl-1-(1H-imidazol-4-ylmethyl)-indan-4-ol $^1$H NMR (as HCl-salt, MeOH-d$_4$): 1.39 (s, 9H), 1.41 (s, 9H), 1.87–1.93 (m, 1H), 2.01–2.06 (m, 1H), 2.66–2.75 (m, 3H), 2.89–2.95 (m, 1H), 3.82–3.89 (m, 1H), 7.15 (s, 1H), 7.33 (s, 1H), 8.77 (s, 1H)

6-tert-Butyl-1-(1H-imidazol-4-yl)-indan-5-ol $^1$H NMR (as HCl-salt, MeOH-d$_4$): 1.32 (s, 9H), 2.06–2.15 (m, 1H), 2.52–2.63 (m, 1H), 2.82–3.02 (m, 2H), 4.46 (t, $_1$H), 6.69 (s, 1H), 6.88 (s, 1H), 7.25 (s, 1H), 8.79 (s, 1H)

4-(6-tert-Butyl-4-methylindan-1-yl)-1H-imidazole. M.p. of hydrochloride 235–242° C.

$^1$H NMR (as HCL-salt, MeOH-d$_4$): 1.25 (s, 9H), 2.09–2.19 (m, 1H), 2.57–2.67 (m, 1H), 2.84–3.07 (m, 2H), 4.55 (t, 1H), 6.91 (s, 1H), 7.12 (s, 1H), 7.25 (s, 1H), 8.74 (s, 1H)

5,7-Di-tert-Butyl-3-(1H-imidazol-4-yl)-indan-4-ol. M.p. of hydrochloride 216–222° C.

$^1$H NMR (as HCl-salt, MeOH-d$_4$): 1.35 (s, 9H), 1.39 (s, 9H), 2.11–2.18 (m, 1H), 2.44–2.52 (m, 1H), 3.06–3.16 (m, 2H), 459–4.63 (m, 1H), 6.78 (s, 1H), 7.23 (s, 1H), 8.75 (s, 1H)

EXAMPLE 15
3-(1H-Imidazol-4-ylmethyl)-indan-5-ol

A stirred mixture of 4-(6-methoxyindan-1-ylmethyl)-1H-imidazole hydrochloride (140 mg) and 48% hydrobromic acid (7 ml) is heated under reflux for 45 minutes. The cooled reaction mixture is poured into water and is made basic with ammonium hydroxide solution. The product is extracted into ethyl acetate which is washed with water, dried with sodium sulfate and evaporated to dryness. The crude product is coverted to its hydrochloride salt in ethyl acetate. M.p. 206–208° C.

$^1$H NMR (as HCl-salt, MeOH-d$_4$): 1.70–1.81 (m, 1H), 2.18–2.29 (m, 1H), 2.70–2.88 (m, 3H), 3.12 (dd, J=15.3 Hz, J=5.8 Hz, 1H), 3.38–3.46 (m, 1H), 6.53 (d, J=2.2 Hz, 1H), 6.60 (dd, J=8.1 Hz, J=2.2 Hz, 1H), 7.01 (d, J=8.1 Hz, 1H), 7.27 (s, 1H), 8.81 (s, 1H)

Using the same method the following compounds were prepared:

1-(1H-Imidazol-4ylmethyl)-indan-5-ol. M.p. of hydrochloride 159–161° C.

$^1$H NMR (as HCl-salt, MeOH-d$_4$); 1.69–1.80 (m, 1H), 2.17–2.29 (m, 1H), 2.71–2.89 (m, 3H), 3.11 (dd, J=14.8 Hz, J=5.7 Hz, 1H), 3.35–3.45 (m, 1H), 6.57 (dd, J=8.1 Hz, J=2.2 Hz, 1H), 6.64 (d, J=2.2 Hz, 1H), 6.89 (d, J=8.1 Hz, 1H), 7.24 (s, 1H), 8.79 (s, 1H)

1(1H-imidazol-4-ylmethyl)-indan-5,6-diol $^1$H NMR (as HCl-salt, MeOH-d$_4$): 1.67–1.78 (m, 1H), 2.15–2.27 (m, 1H), 2.65–2.85 (m, 3H), 3.05 (dd, J=15.1 Hz, J=5.8 Hz, 1H), 3.30–3.40 (m, 1H), 6.51 (s, 1H), 6.63 (s, 1H), 7.24 (s, 1H), 8.80 (s, 1H)

6-tert-Butyl-3-(1H-imidazol-4-ylmethyl)-indan-5-ol $^1$H NMR (as HCl-salt, MeOH-d$_4$): 1.35 (s, 9H), 1.69–1.79 (m, 1H), 2.18–2.28 (m, 1H), 2.69–2.86 (m, 3H), 3.08 (dd, J=15.0 Hz, J=6.0 Hz, 1H), 3.35–3.43 (m, 1H), 6.46 (s, 1H), 7.04 (s, 1H), 7.26 (s, 1H), 8.81 (s, 1H)

6-tert-Butyl-1-(1H-imidazol)-4-ylmethyl)-indan-5-ol. M.p. of hydrochloride 229–230° C.

$^1$H NMR (as HCl-salt, MeOH-d$_4$): 1.32 (s, 9H), 1.72–1.81 (m, 1H), 2.18–2.29 (m, 1H), 2.72–2.87 (m, 3H), 3.03 (dd, J=15.1 Hz, J=6.5 Hz, 1H), 3.32–3.40 (m, 1H), 6.59 (s, 1H), 6.79 (s, 1H), 7.23 (s, 1H), 8.81 (s, 1H)

3-(1H-Imidazol-4-ylmethyl)-6,7-dimethylindan-5-ol. M.p. of hydrochloride 229–238° C.

H NMR (as HCl-salt, MeOH-d$_4$): 1.66–1.78 (m, 1H), 2.08 (s, 3H), 2.13 (s, 3H), 2.14–2.26 (m, 1H), 2.66–2.85 (m, 3H), 3.06 (dd, J=15.1 Hz, J=5.8 Hz, 1H), 3.35–3.43 (m, 1H), 6.39 (s, 1H), 7.22 (s, 1H), 8.79 (s, 1H)

3-(1H-imidazol-4-ylmethyl)-4,7-dimethylindan-5-ol $^1$H NMR (as HCl-salt, MeOH-d$_4$): 1.85–1.93 (m, 1H), 2.07 (s, 3H), 2.11 (s, 3H), 2.11–2.20 (m, 1H), 2.65–2.77 (m, 3H), 2.90 (dd, J=15.1 Hz, J=4.6 Hz, 1H), 3.49–3.57 (m, 1H), 6.47 (s, 1H), 7.19 (s, 1H), 8.79 (s, 1H)

3-[1-(1H-Imidazol-4-yl)-ethyl]-indan-5-ol (mixture of two diastereomers ad and bc)

$^1$H NMR (base, CDCl$_3$+MeOH-d$_4$): 1.12 (d, J=7.0 Hz, —CH$_3$, ad diastereomer), 1.22 (d, J=7.1 Hz, —CH$_3$, bc diastereomer)

3-(1H-Imidazol-4-ylmethyl)-6-methylindan-5-ol $^1$H NMR (as HCl-salt, MeOH-d$_4$): 1.68–1.79 (m, 1H), 2.13 (s, 3H), 2.15–2.27 (m, 1H), 2.68–2.86 (m, 3H), 3.08 (dd, J=15.3 Hz, J=5.8 Hz, 1H), 3.36–3.43 (m, 1H), 6.49 (s, 1H), 6.90 (s, 1H), 7.25 (s, 1H), 8.81 (s, 1H)

1-(1H-imidazol-4-ylmethyl)-indan4-ol. M.p. 199–205° C.

$^1$H NMR (MeOH-d$_4$): 1.68–1.80 (m, 1H), 2.10–2.22 (m, 1H), 2.60–2.86 (m, 3H), 3.00 (dd, J=14.6 Hz, J=5.3 Hz, 1H), 3.38–3.48 (m, 1H), 6.56 (d, J=7.8 Hz, 1H), 6.62 (d, J=7.8 Hz, 1H), 6.71 (s, 1H), 6.94 (t, J=7.8 Hz, 1H), 7.56 (s, 1H)

EXAMPLE 16

4-(1,2,3,4-Tetrahydronaphthalen-1-ylmethyl)-1H-imidazole

The procedure of Example 12 is repeated except that 1-tetralone is used in place of 1-indanone. The melting point of the hydrochloride salt is 185–188° C.

$^1$H NMR (as HCl-salt, MeOH-d$_4$): 1.59–1.93 (m, 4H), 2.70–2.80 (m, 2H), 2.96 (dd, J=14.8 Hz, J=9.5 Hz, 1H), 3.08–3.22 (m, 2H), 7.08–7.14 (m, 4H), 7.25 (s, 1H), 8.81 (s, 1H)

Using the same method the following compounds were prepared:

4-(5-Methoxy-1,2,3,4-tetrahydronaphthalen-1-ylmethyl)-1H-imidazole. M.p. of hydrochloride 210–218° C.

$^1$H NMR (as HCl-salt, MeOH-d$_4$): 1.58–1.64 (m, 1H), 1.71–1.86 (m, 3H), 2.50–2.60 (m, 1H), 2.66–2.74 (m, 1H), 2.96 (dd, J=14.8 Hz, J=9.5 Hz, 1H), 3.05–3.18 (m, 2H), 3.79 (s, 3H), 6.73–6.77 (m, 2H), 7.09 (t, 1H), 7.25 (s, 1H), 8.81 (s, 1H)

4-(6-Methoxy-1,2,3,4-tetrahydronaphthalen-1-ylmethyl)-1H-imidazole M.p. of hydrochloride 184–191° C.

$^1$H NMR (as HCl-salt, MeOH-d$_4$): 1.58–1.88 (m, 4H), 2.70–2.76 (m,2H), 2.93 (dd, J=14.5 Hz, J=9.2 Hz, 1H), 3.04–3.32 (m, 2H), 3.74 (s, 3H), 6.63 (d, J=2.5 Hz, 1H), 6.69 (dd, 8.4 Hz, J=2.5 Hz, 1H), 7.03 (d, J=8.4 Hz, 1H), 7.24 (s, 1H), 8.81 (s, 1H)

4-(7-Methoxy-1,2,3,4-tetrahydronaphthlalen-1-ylmethyl)-1H-imidazole. M.p. of hydrochloride 180–183° C.

$^1$H NMR (as base, CDCl$_3$) 1.59–1.82 (m, 4H), 2.64–2.68 (m, 2H), 2.85 (dd, J=14.6 Hz, J=9.3 Hz, 1H), 3.01 (dd, J=14.6 Hz, J=4.8 Hz, 1H), 3.12–3.17 (m, 1H), 3.72 (s, 3H), 6.68–6.71 (m, 2H), 6.78 (s, 1H), 6.97–7.00 (m, 1H), 7.56 (s, 1H)

4-(4-Methyl-1,2,3,4-tetrahydronaphthalen-1-ylmethyl)-1H-imidazole The product is the mixture of two isomers ad and bc (85% ad and 15% bc).

$^1$H NMR (as HCl-salt, MeOH-d$_4$): 1.25 (d, J=7.0 Hz, —CH$_3$, bc isomer), 1.30 (d, J=7.0 Hz, —CH$_3$, ad isomer), 1.50–2.10 (m, 4H), 2.80–3.04 (m, 2H), 3.10–3.20 (m, 2H), 7.10–7.26 (m, 5H), 8.83 (s, 1H)

EXAMPLE 17

4-(7-tert-Butyl-6-methoxy-1,2,3,4-tetrahydronaphthalen-1-ylmethyl)-1H-imidazole

Sulfuric acid (0.75 ml) is added into the mixture of 4-(6-methoxy-1,2,3,4-tetrahydronaphthalen-1-ylmethyl)-1H-imidazole hydrochloride (75 mg) and tert-butanol (3 ml). The mixture is stirred at 35–40° C. for 15 hours. The reaction mixture is poured into water and is made alkaline with sodium hydroxide. The product is extracted into methylene chloride which is washed with water, dried with sodium sulfate and evaporated to dryness. The residue consisting of crude product is coverted to its hydrochloride salt in ethyl acetate. The yield is 40 mg.

$^1$H NMR (as HCl-salt, MeOH-d$_4$): 1.28 (s, 9H), 1.65–1.95 (m, 4H), 2.70–2.80 (m, 2H), 2.87–3.10 (m, 3H), 3.78 (s, 3H), 6.63 (s, 1H), 6.79 (s, 1H), 7.22 (s, 1H); 8.81 (s, 1H)

EXAMPLE 18

5-(1H-Imidazol-4-ylmethyl)-5,6,7,8-tetrahydronaphthalen-2-ol

A stirred mixture of 4-(6-methoxy-1,2,3,4-tetrahydronaphthalen-1-ylmethyl)-1H-imidazole (220 mg) and 48% hydrobromic acid (11 ml) is heated under reflux for one hour. The cooled reaction mixture is poured into water and is made basic with ammonium hydroxide solution. The product is extracted into ethyl acetate which is washed with water, dried with sodium sulfate and evaporated to dryness. The crude product is converted to its hydrochloride salt in ethyl acetate. The yield is 130 mg, m.p. 200–205° C.

$^1$H NMR (as HCl-salt, MeOH-d$_4$): 1.54–1.90 (m, 4H), 2.62–2.72 (m, 2H), 2.88–3.11 (m, 3H), 6.51 (d, J=2.5 Hz, 1), 6.56 (dd, J=8.3 Hz, J=2.5 Hz, 1H), 6.94 (d, J=8.3 Hz, 1H), 7.23 (s, 1H), 8.81 (s, 1H)

Using the same method the following compound was prepared:

8-(1H-Imidazol-4-ylmethyl)-5,6,7,8-tetrahydronaphthalen-2-ol. M.p. of hydrochloride 245–251° C.

$^1$H NMR (as HCl-salt. MeOH-d$_4$): 1.53–1.89 (m, 4H), 2.60–2.70 (m, 2H), 2.90–2.99 (m, 1H), 3.05–3.12 (m, 2H), 6.55–6.60 (m, 2H), 6.90 (d, J=8.0 Hz, 1H), 7.24 (s, 1H), 8.80 (s, 1H)

What is claimed is:

1. An imidazole derivative compound of formula I

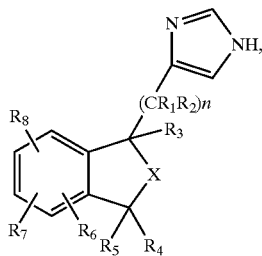

wherein n is 0;

$R_1$ is hydrogen or $C_1$–$C_4$-alkyl;

$R_2$ is hydrogen or $R_2$ and $R_3$ together form a double bond;

$R_3$ is hydrogen or $C_1$–$C_4$-alkyl or $R_2$ and $R_3$ together form a double bond;

$R_4$ is hydrogen, $C_1$–$C_4$-alkyl, hydroxy or $C_1$–$C_4$-alkoxy;

$R_5$ is hydrogen or $C_1$–$C_4$-alkyl or $R_4$ and $R_5$ together with the carbon atom to which they are attached form a carbonyl group;

$R_6$, $R_7$ and $R_8$ are each the same or different and are independently hydrogen, $C_1$–$C_4$-alkyl or $C_2$–$C_4$-alkenyl, $C_3$–$C_7$-cycloalkyl, hydroxy, $C_1$–$C_4$-alkoxy, $C_1$–$C_4$-hydroxyalkyl, thiol, $C_1$–4-alkylthio, $C_{1-4}$-alkylthiol, halogen, trifluoromethyl, nitro, unsubstituted amino, or amino substituted with $C_1$–$C_4$-alkyl;

X is —$CHR_9$—$(CHR_{10})_m$—;

m is 0 or 1; and $R_9$ and $R_{10}$ are each the same or different and are independently hydrogen or $C_1$–$C_4$-alkyl;

or a pharmaceutically acceptable ester or salt thereof, with the proviso that $R_6$, $R_7$, and $R_8$ are not hydrogen, $C_1$–$C_4$-alkyl, hydroxy, $C_1$–$C_4$-alkoxy, and/or halogen when $R_3$, $R_4$ and $R_5$ are all hydrogen.

2. A compound according to claim 1, wherein m=0.

3. A compound according to claim 1, wherein $R_6$, $R_7$ and $R_8$ are each hydrogen.

4. A compound according to claim 2, wherein $R_6$, $R_7$ and $R_8$ are each hydrogen.

5. A compound according to claim 1, wherein $R_6$ is $C_1$–$C_4$-alkyl at position 4 or 6 of the indane ring and $R_7$ and $R_8$ are hydrogen.

6. A compound according to claim 2, wherein $R_6$ is $C_1$–$C_4$-alkyl at position 4 or 6 of the indane ring and $R_7$ and $R_8$ are hydrogen.

7. A compound according to claim 1, wherein $R_6$ is $C_1$–$C_4$-alkoxy at position 7 of the indane ring and $R_7$ and $R_8$ are hydrogen.

8. A compound according to claim 2, wherein $R_6$ is $C_1$–$C_4$-alkoxy at position 7 of the indane ring and $R_7$ and $R_8$ are hydrogen.

9. A composition comprising at least one compound according to claim 1 and a pharmaceutically acceptable carrier.

10. A method for the treatment of hypertension, glaucoma, chronic or acute pain, migraine, diarrhea, common cold, ischemia, addiction to one or more chemical substances, anxiety, or of one or more neurological, musculoskeletal, psychiatric or cognition disorders, which comprises administering to a subject in need of such treatment an effective amount of at least one compound according to claim 1.

11. A method according to claim 10, wherein the treatment is for chronic or acute pain.

12. A method for the treatment of preoperative anxiety, which comprises administering to a subject in need of such treatment an effective amount of at least one compound according to claim 1.

13. A method for potentiating anesthesia, which comprises administering to a subject in need of such potentiated anesthesia an effective amount of at least one compound according to claim 1.

14. A method for activating alpha2-receptors, which comprises administering to a subject in need of such activation an effective amount of at least one compound according to claim 1.

15. A method for the treatment of hypertension, glaucoma, chronic or acute pain, migraine, diarrhea, common cold, ischemia, addiction to one or more chemical substances, anxiety, or of one or more neurological, musculoskeletal, psychiatric or cognition disorders, wherein the method comprises binding alpha2-receptors with an alpha2-receptor agonist, wherein the agonist comprises a compound according to claim 1.

16. A method for the treatment of preoperative anxiety, which comprises binding alpha2-receptors with an alpha2-receptor agonist, wherein the agonist comprises a compound according to claim 1.

17. An imidazole compound, which is
4-(indan-1-yl)-1H-imidazole,
4-(4-methylindan-1-yl)-1H-imidazole,
4-(6-methylindan-1-yl)-1H-imidazole, or
4-(5-chloro-1,2,3,4-tetrahydronaphthalen-1-yl)-1H-imidazole.

18. A method for the treatment of glaucoma, chronic or acute pain, migraine, diarrhea, common cold, addiction to a chemical substance, anxiety, or of one or more neurological, musculoskeletal, psychiatric or cognition disorders, which comprises administering to a subject in need to such treatment an effective amount of at least one imidazole compound of formula I

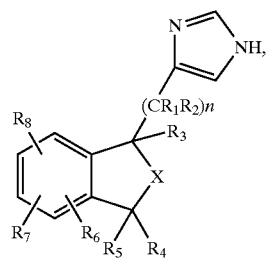

wherein n is 0;

$R_1$ is hydrogen or $C_1$–$C_4$-alkyl;

$R_2$ is hydrogen or $R_2$ and $R_3$ together form a double bond;

$R_3$ is hydrogen or $C_1$–$C_4$-alkyl or $R_2$ and $R_3$ together form a double bond;

$R_4$ is hydrogen, $C_1$–$C_4$-alkyl, hydroxy or $C_1$–$C_4$-alkoxy;

$R_5$ is hydrogen or $C_1$–$C_4$-alkyl or $R_4$ and $R_5$ together with the carbon atom to which they are attached form a carbonyl group;

$R_6$, $R_7$ and $R_8$ are each the same or different and are independently hydrogen, $C_1$–$C_4$-alkyl or $C_2$–$C_4$-alkenyl, $C_3$–$C_7$-cycloalkyl, hydroxy, $C_1$–$C_4$-alkoxy, $C_1$–$C_4$-hydroxyalkyl, thiol, $C_{1-4}$alkylthio, $C_{1-4}$-alkylthiol, halogen, trifluoromethyl, nitro, unsubstituted amino, or amino substituted with $C_1$–$C_4$-alkyl;

X is —$CHR_9$—$(CHR_{10})_m$—;

m is 0 or 1;

and $R_9$ and $R_{10}$ are each the same or different and are independently hydrogen or $C_1$–$C_4$-alkyl;

or a pharmaceutically acceptable ester or salt thereof.

* * * * *

UNITED STATES PATENT AND TRADEMARK OFFICE
CERTIFICATE OF CORRECTION

PATENT NO.   : 6,479,530 B2
DATED        : November 12, 2002
INVENTOR(S)  : Karjalainen et al.

Page 1 of 1

It is certified that error appears in the above-identified patent and that said Letters Patent is hereby corrected as shown below:

<u>Column 23,</u>
Line 32, "$C_1$-4-alkylthio" should read -- $C_{1-4}$-alkylthio --.

<u>Column 24,</u>
Line 47, "need to" should read -- need of --.

<u>Column 25,</u>
Line 10, "$C_{1-4}$alkylthio" should read -- $C_{1-4}$-alkylthio --.

Signed and Sealed this

Twenty-fifth Day of February, 2003

JAMES E. ROGAN
*Director of the United States Patent and Trademark Office*